United States Patent
Woog

[19]

[11] Patent Number: 6,145,468

[45] Date of Patent: Nov. 14, 2000

[54] SILVER INDICATOR METHODS AND TEST KIT

[76] Inventor: Manfred J. Woog, 1040 Pershing St., Craig, Colo. 81625

[21] Appl. No.: 09/174,694

[22] Filed: Oct. 19, 1998

[51] Int. Cl.[7] ........................... G01D 21/00; G01N 33/20
[52] U.S. Cl. ............................................... 116/206; 436/80
[58] Field of Search ............................. 436/6, 80, 164, 436/183, 182; 422/50, 53, 68.155, 61, 82.05; 423/34; 116/206

[56] References Cited

U.S. PATENT DOCUMENTS

| | | | |
|---|---|---|---|
| 2,767,063 | 10/1956 | Chesney | 436/177 |
| 3,625,844 | 12/1971 | McKean | 204/140 |
| 3,661,532 | 5/1972 | Schmitt et al. | 23/230 |
| 3,853,716 | 12/1974 | Yates et al. | 204/28 |
| 3,958,317 | 5/1976 | Peart et al. | 29/195 |
| 4,088,544 | 5/1978 | Hutkin | 204/12 |
| 4,197,275 | 4/1980 | Parker | 423/34 |
| 4,220,320 | 9/1980 | LeGrange | 266/170 |
| 4,309,186 | 1/1982 | Kiefer | 23/230 R |
| 4,384,889 | 5/1983 | Wiewiorowski et al. | 75/101 R |
| 4,740,244 | 4/1988 | Williams | 75/109 |
| 5,456,817 | 10/1995 | Hino et al. | 205/125 |
| 5,993,668 | 11/1999 | Duan | 210/713 |

FOREIGN PATENT DOCUMENTS

| | | |
|---|---|---|
| 936146 | 7/1948 | France . |
| 50-21298 | 7/1975 | Japan . |

OTHER PUBLICATIONS

L. Makhloufi et al., *Electrochim Acta*, 1992, vol. 37, pp. 1779–1786.

N. Klaus, *J. Vac. Sci. Technol.*, 1981, vol. 19, pp. 201–204.

F.J. Hughes et al., *Aust. J. Chem.*, 1984, vol. 37, pp. 903–910.

A.V. Kocherova et al., *Zavod. Lab*, 1976, vol. 42., pp. 1353–1355.

W. Rzeszutko, *Chem. Anal.*, 1974, vol. 19, pp. 81–87.

E.A. Von Hahn et al., *Trans. Met. Soc. AIME*, 1967, vol. 239, pp. 1895–1900.

C. Hennart, *Talanta*, 1965, vol. 12, pp. 694–696.

T.E. Brehmer, *Chem. Abstract*, 1957, vol. 51, pp. 6393f.

R. Glicksman et al., *J. Electrochem. Soc.*, 1953, vol. 12, pp. 580–585.

B.S. Evans, *Chem. Abstract*, 1926, vol. 20, p. 1772.

Environmental Reclamation Ltd.—Advertisement for "5 ppm Silver Indicating Field Test Kit".

*Primary Examiner*—G. Bradley Bennett
*Assistant Examiner*—Gail Verbitsky
*Attorney, Agent, or Firm*—Diane R. Meyers; Eckert Seamans Cherin & Mellott, LLC

[57] ABSTRACT

A method for determining silver concentration in a solution is disclosed. This method generally comprises immersing a substantially pure, elemental, copper strip in a sample of the solution to be tested, agitating the strip in the sample, removing the strip from the sample, and observing the color change, if any, of the strip. These strips are generally greater than 99% pure copper, and have been coated with a metal ion layer. An alternative embodiment provides for removal of the metal ion layer immediately before testing the silver concentration of the solution. A test kit comprising the active copper strips is also disclosed.

15 Claims, 3 Drawing Sheets

SILVER INDICATOR METHODS AND TEST KIT

This application is a CIP of Ser. No. 08/762,111 Dec. 5, 1996 abandoned.

FIELD OF THE INVENTION

The present invention generally relates to a method for determining silver concentration in a solution.

BACKGROUND INFORMATION

Federal, state and local governmental bodies reacting to constituent pressures have instituted a series of laws and regulations aimed at preventing the continued contamination of the environment. These laws and regulations encompass numerous minerals and chemicals regarded as contaminants and/or hazardous materials, and affect many different industries. The content of these minerals and chemicals in effluent streams is often restricted to very stringent levels. Compliance with the increasingly stringent regulations is one of the greatest challenges for industry to meet. Such compliance can become extremely costly, even to a point where competitive pricing can be jeopardized.

Dissolved silver ($Ag_2$) is one hazardous material that is regulated by the Environmental Protection Agency (EPA). The EPA effluent limit for silver in water is 5 ppm or below. It is therefore important that industries discharging or otherwise generating solutions or waste water containing dissolved silver monitor for this low silver concentration.

A variety of methods and devices are available to test effluent solutions for contaminants. For example, for testing the concentration of silver in photo processing and industrial solutions or waste waters various methods and devices have been disclosed using such things as silver sensitive testing papers, copper strips or wire, color metric titration, spectrography and atomic absorption.

Many of these previously disclosed devices can be extremely complex and expensive to employ. Some can only be used under exacting laboratory conditions. In addition, generic copper strips used in other methods vary in quality and can quickly oxidize thereby leading to inconsistent and unreliable results. These factors contribute to inconsistent readings and test performance.

There remains a need, therefore, for simple, low cost, reliable methods and devices that can be readily and remotely employed to test for silver as a contaminant in various industrial solutions and waste waters, particularly those dealing with photo processing. Such methods and devices should be sensitive to low concentrations of silver, particularly those at or near compliance levels.

SUMMARY OF THE INVENTION

The present invention addresses the above defined needs by providing simple, quick and low-cost methods and devices to test for low limits of silver. The methods of the present invention can be employed to determine silver concentration in industrial solutions or waste waters suspected of containing dissolved silver, and are particularly applicable to the detection of silver in photo processing solutions and/or waste waters. The methods are sensitive to the part per million (ppm) range, and silver concentrations of less than about 5 ppm can be determined. The methods and devices disclosed herein have the further advantage of being easily portable, and thus can be used in the field.

It is therefore an object of the present invention to provide a simple, low-cost and easy to use method for determining silver concentration in photo processing and other industrial solutions and waste waters.

It is another object of the present invention to provide a method for testing for silver concentrations below a predetermined concentration.

It is another object of the present invention to provide a method for testing for silver concentrations at or above a predetermined concentration.

Yet another object of the invention is to provide a device for testing for silver concentrations in photo processing and other industrial solutions and waste waters.

It is a further object of the present invention to provide a system that can be used by semi-skilled or unskilled workers.

A further object of the invention is to provide such a device that can be used to determine silver concentrations below a predetermined concentration.

Another object of the invention is to provide such a device for determining silver concentrations at or above a predetermined concentration.

It is a further object of the present invention to provide a device that can be used to determine whether silver concentrations in a solution are greater than or less than 5 ppm.

Another object of the invention is to provide a device for determining silver concentrations that is portable and can be easily used as a field kit.

These and other objects of the invention will be more fully understood by reviewing the following disclosure and claims.

DETAILED DESCRIPTION OF THE INVENTION

Figure 1:
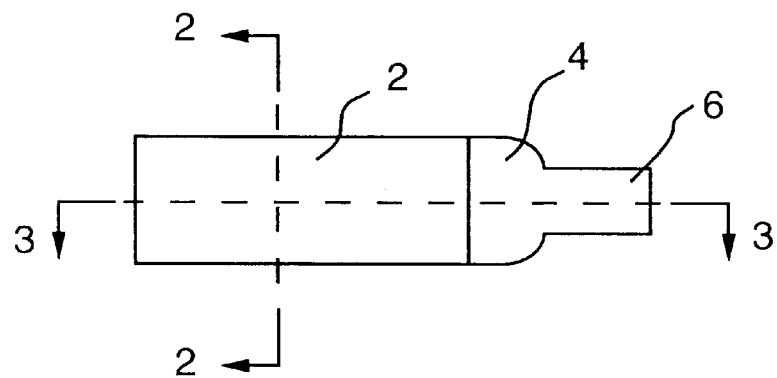
FIG. 1 is a plan view of a copper strip attached to a substrate with a handle according to one embodiment of this invention.

The present invention is directed to a method for determining silver concentration in a solution, generally comprising the steps of obtaining a sample of the solution to be tested; immersing a strip of substantially pure, elemental, copper coated with a metal ion into said solution; removing the strip from the solution sample; observing the color of the strip after it is removed from the solution sample; and employing the color to determine the silver concentration. In a preferred embodiment, the step of agitating the strip in the solution sample for a period of between about 15 and 25 seconds, preferably 20 seconds, is employed and the color of the strip is compared with colors that indicate the concentration of silver in the solution. The concentration of silver can therefore be determined in this manner, as is further described below.

In another embodiment of the present invention, the substantially pure elemental copper coated with a metal ion is first dipped into a solution that removes the metal ion layer. This step is effected immediately prior to the immersion of the strip into the sample to be tested. In this manner, it is the substantially pure copper, without the metal ion layer, that is in direct contact with the solution to be tested. The solution can be any solution that will remove the metal ion layer, referred to herein as the "removing solution". Preferred for this purpose is a dilute acid solution. More preferred embodiments utilize a sodium bisulfate solution or an acetic acid solution. For example, a dilute acid solution suitable for use in the present invention can be prepared by mixing about 50 grams of sodium bisulfate in one liter of deionized water. The metal coated copper strip should be immersed in the removing solution for a time sufficient to effect removal of the metal ion layer. Typically, a time of between about 15 and 25 seconds is preferred, more preferably about 20 seconds. Gentle agitation is preferred when removing the ion layer from the strip. For example, the strip can be moved back and forth between a first and second point every second. In this embodiment, therefore, the copper strips are protected from oxidation by the metal ion layer, but the metal ion layer is removed immediately prior to the determination of silver concentration.

The methods of the present invention can be used to determine the silver concentration in solutions and/or waste waters generated by a variety of industries. The methods will find particular application in the photo processing industry, which typically generates silver as a by-product or waste product.

One advantage of the present methods is that they provide reliable and sensitive results and can be employed easily in the field. Thus, a quick and inexpensive field analysis can be made on a frequent basis by the operators of industrial processes that discharge silver. The analysis provided by the present invention is specifically useful in determining an estimate of silver concentrations, such as whether the silver concentration is above or below a certain concentration. The methods are not intended to be a substitute for the more accurate, and also more costly, quantitative laboratory analysis, such as analysis with atomic absorption, but rather supplement such testing by providing immediate, low cost feedback on silver concentrations. It is a further advantage of the present invention that the sample of solution to be tested does not need to be pre-treated in any way. In addition, when the removing solution is employed to remove the metal ion layer from the substantially pure elemental copper strip prior to testing for silver concentration, the consistency of results obtained from one test to another is enhanced. Also, the sensitivity of the result is enhanced.

The copper strip can be used alone, or it can be attached to a substrate, as is shown in FIG. 1. For example, the copper strip 2 can be attached to a substrate made of fiberglass, resinous plastic or any other suitable material 4. Preferably, the substrate has a handle 6 integrally formed therein. to facilitate handling of the strip throughout the testing procedure.

The copper strips 2 can be of any dimension. Preferred dimensions are between about 0.20 inches to 0.40 inches, preferably 0.30 inches wide, and between about 1.0 inches and 2.5 inches, preferably 1.75 inches long by between about 0.002 inches and 0.006 inches, preferably 0.004 inches thick.

It is preferred that the copper strip 2 used in the methods disclosed herein be made of substantially pure, elemental copper. Substantially pure elemental copper, as used herein, refers to copper that is at least about 99% pure. Preferably, the copper used is even greater than 99% pure. Thus, it will be appreciated that copper alloys are generally unsuitable for the present methods. In addition, the copper used is preferably an unannealed copper. Annealed copper generally contains annealing oils that would interfere with the sensitivity of the copper strip. Alternatively, annealed copper that has been cleaned by suitable methods can be used. This adds unnecessary time and expense to the procedure, however.

The copper purity required here can be achieved by subjecting a raw material containing copper to an electrowinning process. Electrowinning, in the context of the present invention as will be understood by one skilled in the art, is a process by which elemental metals are recovered from solution by an electroplating process. In the electrowinning cell design, one or more rotating cathodes are placed in an open tank with anodes of impure copper. By using this procedure, a sheet of pure copper is formed on the rotating cathode. The side of the sheet facing the cathode is of a generally smooth texture, while the side facing the anode is a rougher texture. It is the smooth side that is preferably used in the determination of silver concentration. The sheet can undergo intermediate processes to achieve the desired shape and dimensions. If the copper strips made from this sheet are affixed to a substrate, it should be attached to the rough side of the copper strip.

The pure copper strip is then subjected to a passivation procedure in which metal ions are deposited on both sides of the strip. Passivation refers to the process of forming a protective film on a metal. Here, passivation protects against the premature oxidation of the copper and therefore helps to ensure that quality consistent material is used in the methods. Passivation is effected by an electrolysis plating action in a bath of the metal ions. This is a self limiting application; that is, only a limited amount of metal can be deposited because a bath containing a fairly low metal ion concentration and low current are used in the electrolysis procedure. Any other suitable means for coating the copper strip with the metal can be used. Any suitable non-copper metal ion that will protect the metal from oxidation but will not interfere with silver determination can be deposited on the copper strip, including but not limited to chromium and iron. Chromium is preferred. More preferably, the metal ion containing bath is an aqueous hexavalent chromate solution. This solution can be prepared by dissolving no more that about 0.5 gram of dichromate in 1.0 liter of purified water. The coated or deposited metal layer should be thick enough to resist oxidation of the copper strip, but thin enough so as not to interfere with determining silver concentration. It will be understood that a thin metal ion layer, as taught herein, can be retained on the copper strips during the testing for silver concentration, since the metal ion layer will not interfere with the results. Removal of the layer for enhanced sensitivity and/or consistency of results is preferred.

Figure 2:
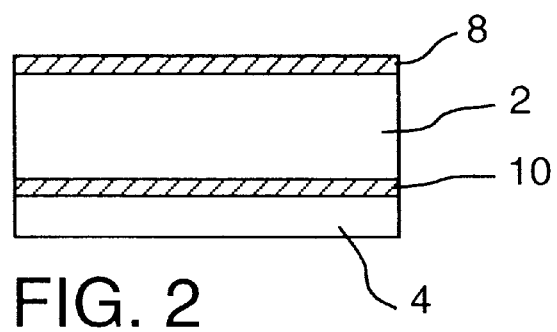
FIG. 2 is a cross sectional view of the copper strip of FIG. 1 taken along lines 2—2.

As will be appreciated by one skilled in the art, and with reference to FIG. 2, the copper strip resulting from this procedure will be a substantially pure elemental copper strip 2, coated on both sides with metal ions 8 and 10. Although the coating appears on both sides, the smooth side of the strip is generally intended to be used for testing silver concentration. As discussed above, because of the electrolysis procedures used to form the copper, one side of the strip typically becomes textured, as contrasted with the generally smooth opposite side; this textured side is more difficult to read and therefore not preferred for use in the present methods.

Figure 3:
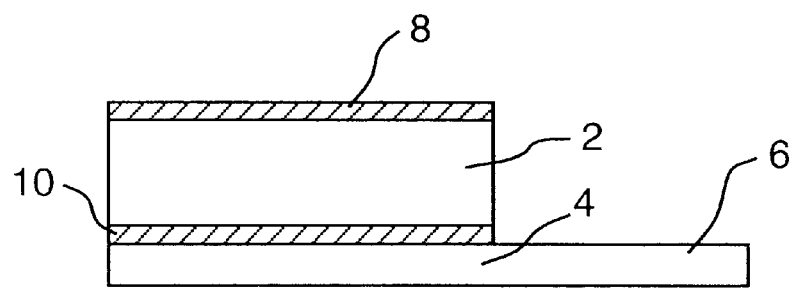
FIG. 3 is a cross sectional view of the copper strip of FIG. 1 taken along lines 3—3.
Figure 4:
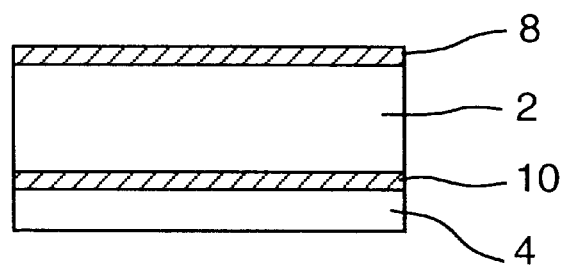
FIG. 4 is an end view of the copper strip of FIG. 1.

FIG. 3 is a cross section of the copper strip 2 of the present invention coated with metal 8 and 10 when used with a substrate 4 having a handle 6. The cross section is taken along the length of the strip. FIG. 4 is an end view of the copper strip 2 of the present invention, taken at the end of the strip 2 opposite the handle 6.

Following preparation of the copper strip, and immediately after removal of the metal ion layer if desired, the strip can then be immersed in a sample of the solution to be tested. Preferably, the strip is not totally immersed in the sample. This provides a place for the strip to be grasped by the hand, forceps, or other suitable instrument, without touching the sample. In addition, partial immersion allows for a portion of the copper strip to remain unreacted with the solution, thereby providing a basis for comparison between the reacted and unreacted copper.

As stated above, the sample, which should generally be an aqueous based solution, does not need to be treated in any way before the copper strip is immersed. Again, removal of the metal ion layer can optimally be performed. It is important, however, that before obtaining a sample of the solution to be tested that the user's hands and the container in which the sample is collected are free from any silver containing solutions. Otherwise, contamination can result and the silver measurement would be inaccurate. The copper strip should be immersed for a period of time sufficient to determine whether a predetermined amount of silver is in a solution. Preferably, for a method that tests for silver concentrations above or below 5 ppm, the time for immersion is between about 15 and 25 seconds, more preferably about 20 seconds. If the immersion time is less than this range, this may not provide sufficient time for an accurate measurement of the silver concentration to be recorded. Similarly, an immersion time of greater than this range may provide too much time for silver concentration to be recorded. The preferred time of about 20 seconds reflects the standard silver concentrations obtained when comparing results of the present methods with those obtained by atomic absorption. As will be appreciated by one skilled in the art, the immersion time can be altered outside of the disclosed range so long as the standardization parameters address this alteration and tests are performed in a uniform manner.

During the immersion period, the copper strips are preferably gently agitated in the sample solution, with the strip being moved back and forth at a rate of a move from a first point to a second point per second. As with the time for immersion, agitation can be changed, or even eliminated, so long as the standard reflects this change and tests are performed in a uniform manner.

Following the immersion/agitation of the copper strip, the strip is removed and evaluated for silver concentration. This evaluation should occur almost immediately upon removal of the strip from the sample, and preferably within at least about 10 seconds of removal. The strips should be evaluated promptly after removal because oxidation of the strip will continue to occur following removal from the sample solution. This oxidation would cause the color of the strip to become more intense, which can lead to misinterpretation of results.

Evaluation of the tested strip is generally performed by visual inspection of the strip in which the color of the strip is noted. When testing for silver concentrations of greater than or less than about 5 ppm, the following interpretations can be made. If the strip contains no visible tarnish, silver concentrations are below about 5 ppm; if the strip has a light shadow of tarnish that is light gray to brown in color, silver concentrations are at or above 5 ppm; and if the strip has a strong tarnish that is dark gray to silver in color, silver concentrations are much higher than about 5 ppm. Thus the methods of the present invention can be used to make a quick and reliable determination of whether silver concentrations are near or below accepted EPA standards. This tarnish, if formed, is actually a layer of silver that deposits on the copper strip.

Figure 5:
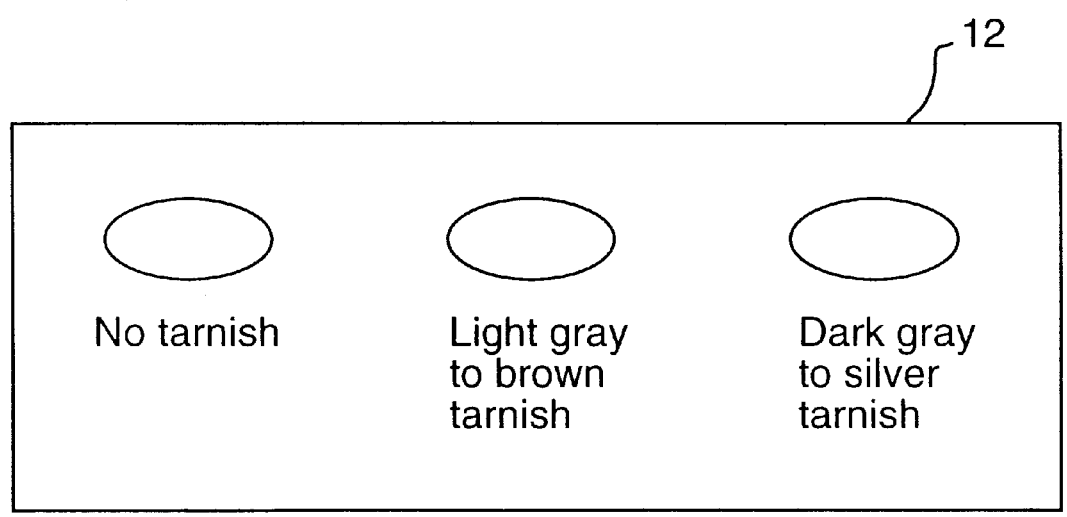
FIG. 5 is a color standard chart for use according to the methods of the present invention.

A tarnish color standard chart as illustrated in FIG. 5 can also be used in conjunction with the methods as described above. Such a chart 12 would indicate what color of tarnish to look for in determining which silver concentration is present. Use of a color chart would help to avoid any possible misinterpretations in the tarnish color of the tested copper strip. FIG. 5 illustrates the use of the invention wherein a color standard chart 12 is used. The tarnish color obtained following testing with copper strip 2 shown in FIG. 1 is compared with the tarnish color chart provided in FIG. 5.

Rather than determining the silver concentration by visual inspection, the determination can alternatively be made by the use of a reflective densimetric measurement or other suitable instruments. The output of such instruments could then be delivered to a microprocessor as an electrical signal, with the microprocessor providing an output that is either a function of the silver concentration or the actual silver concentration. The use of such technology will be familiar to one skilled in the art. This embodiment would also be more costly and may not be practical to apply in the field.

The methods described above are generally useful in determining whether silver concentrations are greater than or less than 5 ppm, the EPA accepted level for silver discharge. Similar methodologies can be employed to determine whether silver concentrations are greater than or less than other values of silver such as 10 ppm, 25 ppm, etc. These methodologies would employ the use of different parameters such as different agitation and immersion times, different thickness of starting materials and the like, depending on the concentration for which it is desired to test.

The present invention is also directed to a test kit for determining the concentration of silver in a solution. This test kit comprises an active copper strip which is the same as the copper strip described above. The strip is therefore a substantially pure, elemental, copper strip coated with a metal ion layer created by an electrowinning process that purifies a copper raw material into a pure copper form and passivating the electrowinned strip in a bath containing a metal ion. In one embodiment, the kit can be used to determine silver concentrations of greater than or less than about 5 ppm.

Figure 6:
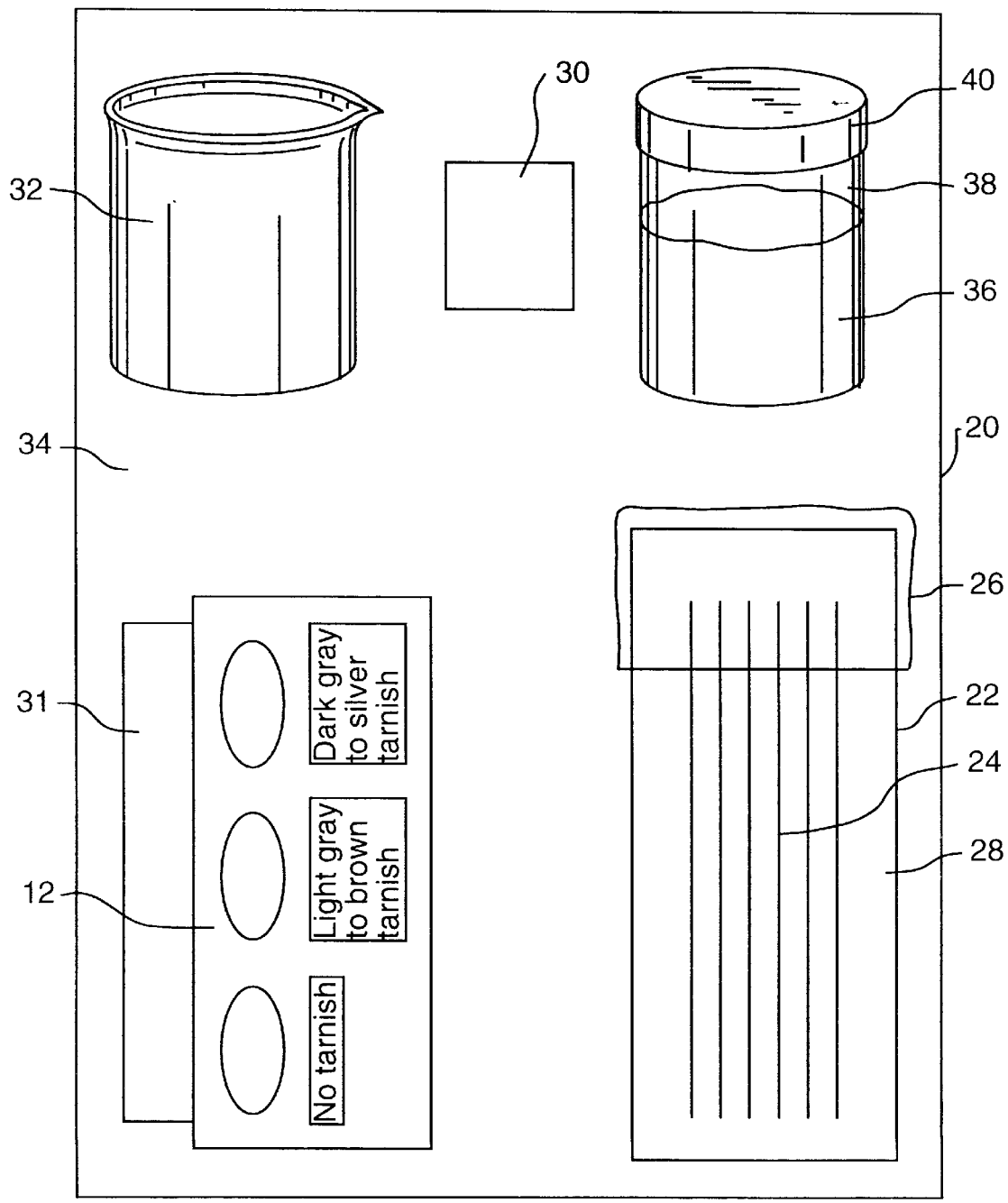
FIG. 6 is a plan view of a silver test kit of one embodiment of the present invention.

The kit, illustrated in FIG. 6, is preferably packaged in a suitable package, more preferably a clear plastic box 20, for example. Any other suitable material could also be used. A smaller package 22 can be used to hold a plurality of the copper strips 24. Again, the smaller package 22 is preferably clear plastic, and has an overfit cap 26 such that a fairly tight seal is created with the packaging; this helps to keep air from oxidizing the strips over the shelf life of the product. A piece of cotton, foam or other suitable material 28 inside the smaller package to further protect the strips from being damaged is also preferred. The kit can also comprise cover labels 30 for use in identification of samples, instructions 31, a small plastic beaker 32 for collecting the sample, and a protective foam 34 or other type of pad to protect the integrity of the kit during shipping. The kit can further comprise a tarnish color standard chart 12 for use in comparing the tested copper strips with colors that indicate the concentration of silver in the solution being tested. In addition, the kit can include a solution 36 for removing the metal ion layer before testing of the silver concentration, contained, for example, in a plastic jar 38 with a spin-on lid 40. Any other liquid sealable container could also be used. It will be appreciated that these features represent preferred embodiments and that components made of other materials are equally within the scope of the invention.

EXAMPLES

The following examples are intended to illustrate the present invention and should not be construed as limiting the invention in any way.

Example 1

A 25 ml sample of a photo processing solution was collected in a clean, 30 ml plastic beaker. The copper strip was immersed in the sample solution, and moved from a first point to a second point at a rate of 1 move per second. After 20 seconds, the copper strip was removed and the color of the strip observed. There was no indication of visible tarnish, indicating a silver concentration of below about 5 ppm.

Example 2

Example 1 was repeated using a different sample of a photo processing solution. A dark gray tarnish appeared on the strip following immersion and agitation in the sample indicating a higher silver concentration than 5 ppm was present in the solution.

Example 3

A 25 ml. sample of a photo processing solution was collected in a clean, 30 ml. plastic beaker. The copper strip was immersed in a removing solution of dilute sodium bisulfate for about 20 seconds with gentle stirring, 1 move per second. The copper strip was removed from the removing solution and immersed in the sample solution. Gentle agitation was employed to move the strip from a first point to a second point at a rate of 1 move per second for about 20 seconds. The copper strip was removed and the color of the strip observed. A light shadow of tarnish, brownish in color, appeared, indicating that the silver concentration of the sample solution was at or above 5 ppm.

It will be understood that the present invention provides silver indicator methods and test kits for determining silver concentrations in solutions and other waste waters. These methods generally utilize a pure elemental copper strip which will tarnish in the presence of silver.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for determining silver concentration in a solution comprising:
   a) immersing a strip of substantially pure, elemental, copper coated with a metal ion layer into a removing solution that removes the metal ion layer;
   b) removing said strip from said removing solution;
   c) immediately immersing said strip into the solution to be tested for silver concentration;
   d) removing said strip from said solution of step c);
   e) observing the color of the tarnish on said strip; and
   f) employing the color of the tarnish in determining the silver concentration.

2. The method of claim 1, wherein said removing solution is a dilute acid solution.

3. The method of claim 1, wherein said removing solution is selected from the group consisting of a dilute sodium bisulfate solution and a dilute acetic acid solution.

4. The method of claim 1, wherein said copper strip is immersed into said removing solution for a period of between about 15 and 25 seconds.

5. The method of claim 1, further including the step of agitating said strip in said solution to be tested for silver concentration following the immersion of step c).

6. The method of claim 5, including agitating said strip for a period of between about 15 and 25 seconds.

7. The method of claim 1, wherein step f) is effected by comparing the color of the tarnish on said strip with colors that indicate the concentration of silver.

8. The method of claim 7, wherein said comparing step is done visually.

9. The method of claim 1, wherein the silver concentration is determined by use of reflective densimetric measurement.

10. The method of claim 1, including creating said coated copper strip by using an electrowinning process that purifies a copper raw material into a pure copper form, and treating said electrowinned copper strip by passivating said strip in a bath of metal ions.

11. The method of claim 10, including employing a bath of metal ions selected from the group consisting of chromium ions and iron ions.

12. The method of claim 11, including employing a bath of an aqueous hexavalent chromate solution.

13. The method of claim 1, wherein said elemental copper is greater than 99% pure.

14. The method of claim 1, including employing said method to determine whether silver concentrations are greater than or less than about 5 ppm.

15. A test kit for determining the concentration of silver in a solution comprising a substantially pure, elemental, copper strip coated with a metal ion layer and a solution for removing the metal ion layer.

* * * * *